(12) United States Patent
Soubeiran (10) Patent No.: US 8,632,548 B2
(45) Date of Patent: Jan. 21, 2014

(54) INTRACORPOREAL ELONGATION DEVICE WITH A PERMANENT MAGNET

(76) Inventor: Arnaud Soubeiran, Paris (FR)

( * ) Notice: Subject to any disclaimer, the term of this patent is extended or adjusted under 35 U.S.C. 154(b) by 929 days.

(21) Appl. No.: 12/444,337

(22) PCT Filed: Oct. 2, 2007

(86) PCT No.: PCT/FR2007/001612
§ 371 (c)(1),
(2), (4) Date: Apr. 3, 2009

(87) PCT Pub. No.: WO2008/040880
PCT Pub. Date: Apr. 10, 2008

(65) Prior Publication Data
US 2010/0049204 A1    Feb. 25, 2010

(30) Foreign Application Priority Data
Oct. 3, 2006    (FR) ...................................... 06 08678

(51) Int. Cl.
*A61B 17/68*    (2006.01)
(52) U.S. Cl.
USPC ............................................................ 606/90
(58) Field of Classification Search
USPC ......... 606/86 R, 87–89, 90, 105, 60, 68, 282, 606/300–331
See application file for complete search history.

(56) References Cited

U.S. PATENT DOCUMENTS

| | | | |
|---|---|---|---|
| 3,976,060 A * | 8/1976 | Hildebrandt et al. ......... | 606/241 |
| 5,704,939 A | 1/1998 | Justin | |
| 5,720,746 A | 2/1998 | Soubeiran | |
| 6,033,412 A * | 3/2000 | Losken et al. ................ | 606/105 |
| 6,200,317 B1 * | 3/2001 | Aalsma et al. ................ | 606/62 |

(Continued)

FOREIGN PATENT DOCUMENTS

| | | |
|---|---|---|
| DE | 85 15 687 | 10/1885 |
| FR | 2901991 | 12/2007 |

(Continued)

OTHER PUBLICATIONS

Verkerke et al., "Design of a lengthening element for a modular femur endoprosthetic system," *Proc Inst Mech Eng [H]*, 1989; 203(2):97-102.

(Continued)

*Primary Examiner* — Christopher Beccia
(74) *Attorney, Agent, or Firm* — Foley Hoag LLP (57) ABSTRACT

A first part (1) comprises means (11) for connection to the body and receives in a sliding manner a second part (2) that comprises means (21) for connection to the body. A permanent magnet (3) is mounted in rotation relative to the first part (1). Step-down gears (51, 52) transform its movements into a rotation, alternately in one direction and in the other, of an input shaft (41) with a gear reduction ratio. A free wheel (43) drives an output shaft (42) when the input shaft (41) turns in one direction. The output shaft (42) is blocked in the other direction by retaining means (44). Transmission means (61, 62) transform the rotation of the output shaft (42) into a displacement of the second part (2) relative to the first part (1). The invention permits the production of bone prostheses allowing growth, of intramedullary nails allowing elongation or movement of bone, of spinal distraction or compression rods, or of bone distractors or intercostal distractors, and also of implantable remote-controlled pumps.

1 Claim, 6 Drawing Sheets

(56) References Cited

U.S. PATENT DOCUMENTS

| | | | |
|---|---|---|---|
| 6,796,984 B2 * | 9/2004 | Soubeiran | 606/300 |
| 6,849,076 B2 * | 2/2005 | Blunn et al. | 606/105 |
| 7,955,357 B2 * | 6/2011 | Kiester | 606/258 |
| 7,981,025 B2 * | 7/2011 | Pool et al. | 600/37 |
| 2005/0246034 A1 | 11/2005 | Soubeiran | |
| 2005/0251109 A1 | 11/2005 | Soubeiran | |
| 2005/0261779 A1 * | 11/2005 | Meyer | 623/23.47 |
| 2009/0254088 A1 | 10/2009 | Soubeiran | |
| 2010/0280519 A1 | 11/2010 | Soubeiran | |

FOREIGN PATENT DOCUMENTS

| | | |
|---|---|---|
| WO | WO-9615377 | 5/1996 |
| WO | WO-9951160 | 10/1999 |
| WO | WO-0042592 | 7/2000 |
| WO | WO-0164119 | 9/2001 |
| WO | WO-0178614 | 10/2001 |
| WO | WO-02056777 | 7/2002 |
| WO | WO-02071962 | 9/2002 |
| WO | WO-2004019795 | 3/2004 |
| WO | WO-2004019796 | 3/2004 |
| WO | WO-2007144489 | 12/2007 |
| WO | WO-2008040880 | 4/2008 |
| WO | WO-2009004157 | 1/2009 |

OTHER PUBLICATIONS

International Search Report and Written Opinion for PCT/FR2007/001612.

* cited by examiner

INTRACORPOREAL ELONGATION DEVICE WITH A PERMANENT MAGNET

CROSS-REFERENCE TO RELATED APPLICATIONS

This is the national stage of International application no. PCT/FR2007/001612, filed Oct. 2, 2007, which claims the benefit of French application no. 06/08678, filed Oct. 3, 2006.

TECHNICAL FIELD

The present invention relates to intracorporeal elongation devices, in particular bone prostheses allowing growth, intramedullary nails for bone elongation, spinal distraction or compression rods or bone distractors or intercostal distractors and, more especially, to those devices that comprise a movable permanent magnet for receiving the energy needed for the elongation by way of a magnetic field source placed outside the body and acting through the part of the body surrounding said device.

PRIOR ART

Several intracorporeal elongation devices comprising a movable permanent magnet for receiving the energy needed for the elongation have been proposed.

Most of them, such as the ones described in documents U.S. Pat. No. 3,976,060, Proc Inst Mech Eng [H], 1989; 203(2): 97-102, U.S. Pat. No. 6,849,076, U.S. Pat. No. 5,704,939 and FR 06/05236, are composed of a first part, which comprises first means of connection to the body, a second part, which comprises second means of connection to the body and is mounted so as to slide relative to said first part, a permanent magnet, means of connection between said permanent magnet and said first part, which means of connection allow said permanent magnet a degree of freedom of rotation about an axis substantially perpendicular to its direction of magnetization, and means for transforming the movements of said permanent magnet into movements of said second part relative to said first part.

In document U.S. Pat. No. 3,976,060, said means of connection between said permanent magnet and said first part of the device described are a lever, which receives said permanent magnet at the end of its longer arm and the shaft about which this lever turns and which is perpendicular to the direction of magnetization of said magnet but is not one of its main axes of inertia. The attraction/repulsion of said permanent magnet by means of a field source, which is placed outside the body and which has successively one pole and the other substantially in the direction of magnetization of said permanent magnet, causes the oscillation of said lever. If said direction of magnetization coincides with the direction in which the distance between said permanent magnet and the outside of the body is shortest, control of said device is made considerably easier. The means for transforming the movements of said permanent magnet into movements of said second part relative to said first part are formed by a catch which is integral with the shorter arm opposite said longer arm of said lever, by a toothed wheel driven by said catch, and by a screw which is integral with said toothed wheel and is in helical connection to said second part and whose rotation therefore moves said second part relative to said first part.

The use of a lever as gear reduction means is advantageous, but this device must remain sealed, especially the volume occupied by the magnet and the lever, but also the catch system, and this is awkward to do over the course of time and limits the possible methods of sterilization. In addition, its general geometry and its lack of solidity limit its mechanical strength and its implantation possibilities.

In the other documents, Proc Inst Mech Eng [H], 1989; 203(2): 97-102, U.S. Pat. No. 6,849,076, U.S. Pat. No. 5,704,939 and FR 06/05236, said permanent magnet turns about one of its main axes of inertia, which is in the form of a component that has a seat for said permanent magnet and that constitutes said means of connection between said permanent magnet and said first part. The elongation of these devices requires said permanent magnet to be driven about 360°. To do this, it is necessary to use an external magnetic field source which surrounds or turns around the whole part of the body containing said device. Said source must be dimensioned in accordance with the greatest diametrical dimension, relative to the axis of rotation of said permanent magnet, of said part of the body containing said device, which is unfavorable in terms of overall size, power, cost, optimization for a given patient, or the ergonomics of said source. All this will be particularly noticeable if the device is, for example, placed along the vertebral column: to surround the thorax or turn around it is much less advantageous than being able to activate the device by placing the source very near in the back.

In documents U.S. Pat. No. 5,704,939 and FR 06/05236, the means for transforming the movements of said permanent magnet into movements of said second part relative to said first part of the described devices are a simple screw which is integral with said means of connection between said permanent magnet and said first part and with an axis that is coincident with the axis of rotation of said permanent magnet. These devices are able to function without a seal and are still simple, but the distraction force produced is limited.

In the documents Proc Inst Mech Eng [H], 1989; 203(2): 97-102 and U.S. Pat. No. 6,849,076, the means described for transforming the movements of said permanent magnet into movements of said second part relative to said first part are formed, not only by a screw, as in documents U.S. Pat. No. 5,704,939 and FR 06/05236, but by a step-down gear interposed between said screw and said means of connection between said permanent magnet and said first part. The distraction force that these devices can produce is high, but said step-down gear is costly, requires specific means of production, is bulky and must remain sealed in order to properly function. Miniaturization of these devices is also highly problematic.

The aims of the intracorporeal elongation device according to the invention are therefore:
  Functioning without a seal, even when attacked by the biological substances produced in its environment, since ensuring the leaktightness of an intracorporeal elongation device remains a difficulty and a point of weakness and limits the possibilities of sterilization.
  A high force of distraction within a modest volume so as to permit use in all types of elongation, especially elongation of the bones, and in all fields, including pediatrics. Since the elongation force produced by an elongation device with magnetic transmission depends, on the one hand, on the force exerted on said permanent magnet by said magnetic field source placed outside the body and, on the other hand, on the step-down gears used, and since the force exerted on said permanent magnet depends on the power of the external magnetic field source but also to a great extent on the distance at which it can be placed relative to said permanent magnet, the device according to the invention will combine simple, compact and powerful step-down gears, with the possibility of controlling said device from the direction, perpendicular to the axis of rotation of said magnet, in which said permanent magnet is closest to the outside of the body.

Good ergonomics, both in order to facilitate its implantation by the surgeon and also its elongation by the patient himself, in most cases done at home, or even while on the move, especially in those treatments, such as elongation of bones, which require elongation at least daily, in particular with external means for controlling the elongation, and use of said means that are safe and adapted to daily use by an unqualified person.

A reasonable cost, which is linked in particular to the number of component parts of the device and to the difficulty of producing them. The systems with a catch, with a gear or a seal will be avoided which require particular production techniques and a particular surface quality, these naturally being more expensive than the ones that comprise a small number of component parts, which can be produced using current manufacturing techniques, all the more so given that the system must have small dimensions. The components of the device according to the invention will therefore be able to be produced in a standard micro-mechanics factory, regardless of the scale at which it will be expedient for said device to be produced.

DISCLOSURE OF THE INVENTION

To do this, the intracorporeal elongation device according to the invention is composed of a first part, which comprises first means of connection to the body, a second part, which comprises second means of connection to the body and is mounted so as to slide relative to said first part, and a permanent magnet, and said device includes:

means of connection between said permanent magnet and said first part, which means of connection allow said permanent magnet a degree of freedom of rotation substantially about one of its main axes of inertia perpendicular to its direction of magnetization, an input shaft, step-down gears for transforming the movements of said permanent magnet into rotation of said input shaft, alternately in a first direction and in the opposite direction, with a gear reduction ratio between the rotation of said input shaft and that of said permanent magnet and such that a change of direction of rotation of said permanent magnet causes the change of direction of rotation of said input shaft, an output shaft, free-wheel means for driving said output shaft in said first direction when said input shaft turns in said first direction, retaining means for preventing the rotation of said output shaft in the direction opposite to said first direction when said input shaft turns in said direction opposite to said first direction, and transmission means such that the rotation of said output shaft causes the displacement of said second part relative to said first part.

Said transmission means can be a first helical connection between a first surface integral with said output shaft and a second surface integral with said second part.

Said step-down gears can be formed by a lever integral with said input shaft, with which it shares the axis of rotation, and means of connection between a first supporting surface, integral with said permanent magnet and remote from its axis of rotation, and a second supporting surface integral with the end of said lever farthest from said axis of rotation common to said lever and to said input shaft.

The rotation of said permanent magnet can be limited to an angle sector of less than 180° by first abutment means in one direction, and by second abutment means in the opposite direction.

Said means of connection between said first supporting surface and said second supporting surface can include a clearance that permits the rotation of said permanent magnet, without driving said lever, on two sectors substantially opposite to each other relative to the axis of rotation of said permanent magnet.

Said step-down gears can alternatively be formed by an amplifying component mounted in translation and blocked in rotation relative to said first part and comprising a third surface in second helical connection to a fourth surface integral with said permanent magnet, and a fifth surface in third helical connection to a sixth surface integral with said input shaft, the axes of rotation of said permanent magnet, of said second and third helical connections and of said input shaft being coincident, the pitches of said second and third helical connections being in said gear reduction ratio of said step-down gears, and the pitch of said second helical connection being sufficiently great relative to the coefficient of friction of said second helical connection to permit the functioning of said step-down gears.

Regardless of its configuration, the device according to the invention will be able to be controlled with the aid of a magnetic field source which is placed outside the body and is able to produce a rotating field, either about the axis of rotation of said permanent magnet or about an axis parallel thereto. Said magnetic field source will be able to be an electromagnetic source but will preferably be a neodymium magnet placed outside the body at the point nearest said permanent magnet and in such a way that one of its main axes of inertia substantially perpendicular to its direction of magnetization is substantially parallel to the axis of rotation of said permanent magnet. Said neodymium magnet will then be set in rotation about this main axis of inertia parallel to the axis of rotation of said permanent magnet. Alternatively, said neodymium magnet will be able to turn all round the part of the body containing said device according to the invention, substantially following the axis of rotation of said permanent magnet and at all times presenting the same pole to the latter. In this case, it may be advantageous for a second neodymium magnet to be maintained sufficiently distant from the first by a structure that can comprise a soft magnetic material, the north pole of one facing the south pole of the other such that it can be arranged outside the body, on either side of said device according to the invention.

One or other of the methods will be more effective depending on the location of the device, the morphology of the patient and the embodiment of the device according to the invention. If, for example, said step-down gears are formed by an amplifying component, said rotating field will then have to make a certain number of turns in one direction, then the same number of turns in the opposite direction in order to control said device according to the invention, and so on, and it will be preferable that this rotation is made about the axis of rotation of said permanent magnet. In this case, it will therefore be preferable to have said neodymium magnet turn all round the part of the body containing said device, at all times presenting the same pole directed toward the axis of rotation of said permanent magnet, except if said part of the body has zones very close to said permanent magnet and others very distant from it. This is the case with a spinal rod, for example, for which it will be preferable to choose either another embodiment of the device or to control the device according to the method in which said neodymium magnet turns about its main axis of inertia parallel to said axis of rotation of said permanent magnet by the number of turns necessary in one direction and then in the other, and so on. If said step-down gears are formed by a lever, the method involving turning said neodymium magnet about its main axis of inertia parallel to said axis of rotation of said permanent magnet will generally be preferred, and the direction of rotation will be of little importance except if said means of connection between said first supporting surface and said second supporting surface comprise a clearance, in which case one direction will produce a distraction force slightly greater than the other direction.

If the rotation of said permanent magnet is limited to an angle sector of less than 180° in one direction by first abutment means and in the opposite direction by second abutment means, the device according to the invention can be controlled by the two methods already described, but also by successively presenting each of the two poles of said magnetic field source substantially in the direction perpendicular to the bisecting direction of the directions in which said direction of magnetization of said permanent magnet is located when the latter is respectively in its position corresponding to said first abutment means and in its position corresponding to said second abutment means.

BRIEF DESCRIPTION OF THE DRAWINGS

The invention, its functioning and its uses will be better understood, and other features and advantages thereof will become clear, from the following description which is given by way of illustration, and without implying any limitation, and in which reference is made to the attached drawings, in which:

FIGS. 1 to 6 show a first preferred embodiment of the device according to the invention, more particularly designed for implantation at the surface of bones, for example along the vertebral column or the jaw or between ribs.

FIGS. 7 to 12 show a second preferred embodiment of the device according to the invention, more particularly designed for implantation in the medullary canal of a long bone for the purpose of elongation or movement of bone. FIGS. 9 and 10 are sectional views passing through the axis of rotation of said permanent magnet. FIG. 10 shows it at the end of elongation.

FIGS. 13 and 14 show a third preferred embodiment of the device according to the invention, particularly useful when the degree of the elongation force produced takes precedence over the control ergonomics.

It will be noted that the same reference signs in the figures designate the same elements, whatever the figure in which they appear and whatever the mode of representation of these elements. Likewise, if an element is not specifically shown in one of the figures, so as not to overcomplicate the figure, its reference sign can be easily found by turning to another figure.

The concealed lines are represented by dots and dashes in all the figures, except in FIGS. 3 to 7 where they are not shown. In all the figures, the dimensions and proportions have been adapted where this was felt to make the figures easier to follow.

The applicant also wishes to stress that the figures show several preferred embodiments of the device according to the invention, but that other embodiments exist that meet the definition of this invention.

The applicant additionally stresses that when, according to the definition of the invention, the device according to the invention comprises "at least one" element having a given function, the embodiment described may comprise several of these elements.

The applicant also stresses that if the embodiments of the subject matter according to the invention, as illustrated, comprise several elements of identical function and if, in the description, it is not specified that the subject matter according to the invention must necessarily comprise a specific number of these elements, the subject matter of the invention can be defined as comprising "at least one" of these elements.

WAYS OF IMPLEMENTING THE INVENTION

All the embodiments of the device according to the invention are composed of:

a first part 1, which comprises first means 11 of connection to the body, a second part 2, which comprises second means 21 of connection to the body and is mounted so as to slide relative to said first part 1, a permanent magnet 3, means of connection between said permanent magnet 3 and said first part 1, which means of connection allow said permanent magnet 3 a degree of freedom of rotation substantially about one of its main axes of inertia perpendicular to its direction of magnetization, an input shaft 41, step-down gears for transforming the movements of said permanent magnet 3 into rotation of said input shaft 41 alternately in a first direction and in the opposite direction with a gear reduction ratio between the rotation of said input shaft 41 and that of said permanent magnet 3 and such that a change of direction of rotation of said permanent magnet 3 causes the change of direction of rotation of said input shaft 41, an output shaft 42, free-wheel means 43 for driving said output shaft 42 in said first direction when said input shaft 41 turns in said first direction, retaining means 44 for preventing the rotation of said output shaft 42 in the direction opposite to said first direction, and transmission means such that the rotation of said output shaft 42 causes the displacement of said second part 2 relative to said first part 1.

Moreover, in all the preferred embodiments shown in FIGS. 1 to 14, said transmission means are a first helical connection between a first surface 61 integral with said output shaft 42 and a second surface 62 integral with said second part 2.

In the first preferred embodiment of the device shown in FIGS. 1 to 6, said first part 1 is formed substantially by a tube 12 which is continued at one of its ends by a rod 11 that constitutes said first means 11 of connection to the body. A screw 62, of which the external diameter corresponds substantially to the internal diameter of said tube 12 and which is continued by a rod constituting said second means 21 of connection to the body, forms said second part 2.

Figure 1:
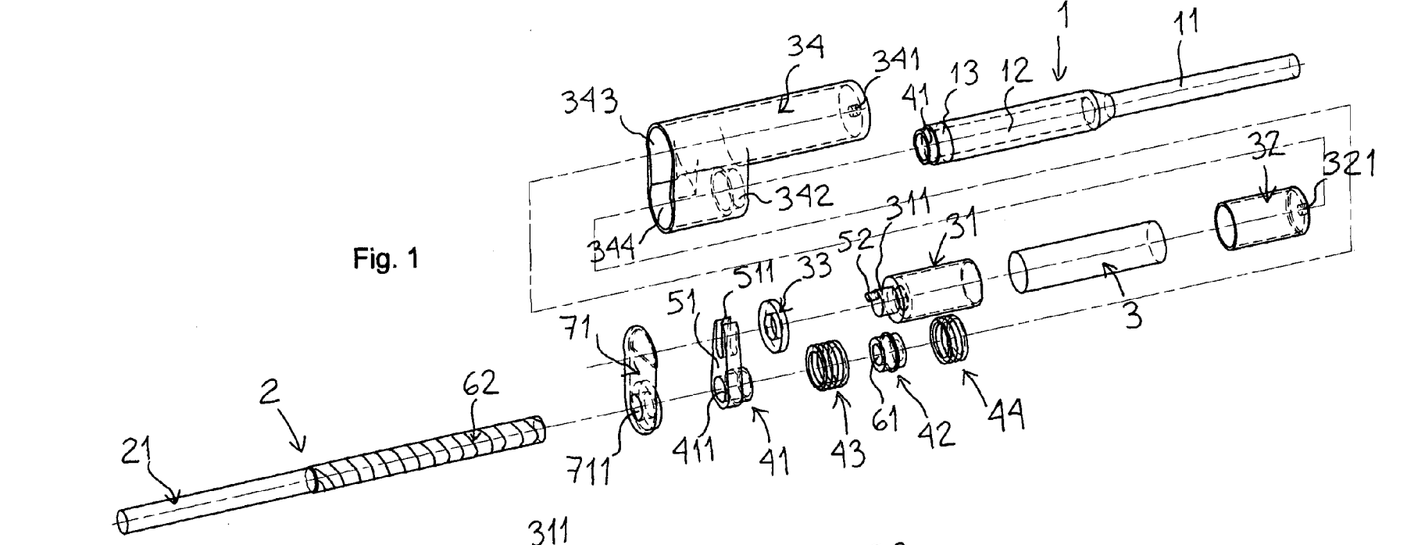
FIG. 1 is an exploded perspective view of this embodiment.
Figure 2:
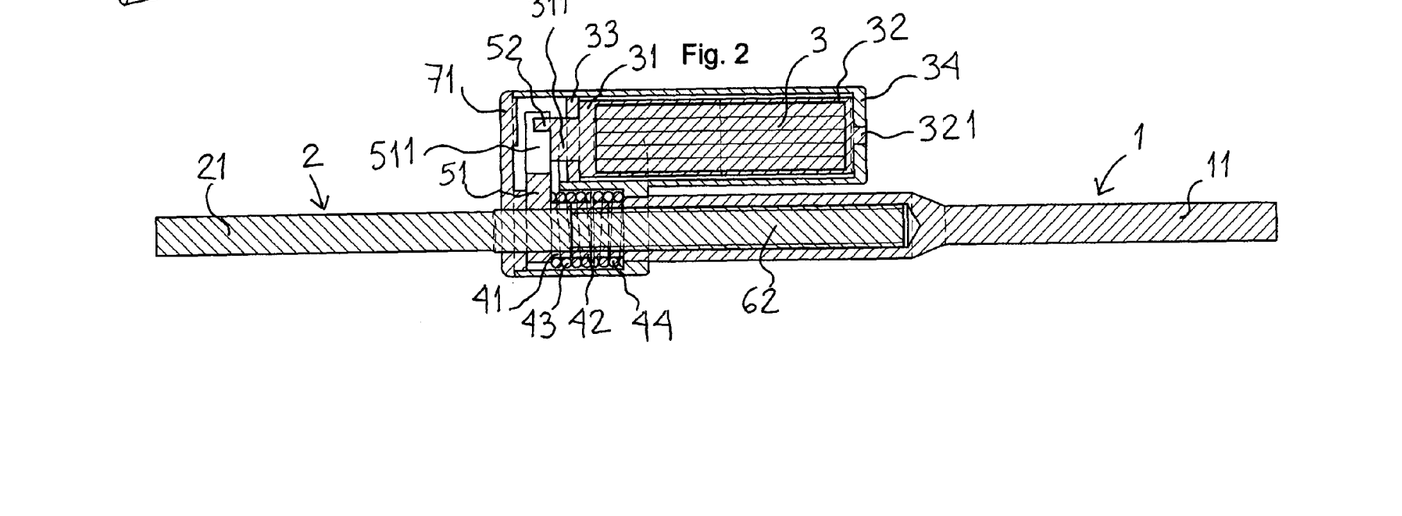
FIG. 2 is a sectional view passing through the axes of rotation of said permanent magnet and of translation of said second part relative to said first part, and in which said device is shown in its shortened position.

The permanent magnet 3 is cylindrical, magnetized diametrically and bonded, for example with the aid of a silicone adhesive, to the inside of first 31 and second 32 caps which are arranged head to tail and which, at the end opposite the one in which said permanent magnet 3 is inserted, are continued, respectively, by a first shaft 311, which forms the axis of rotation of said permanent magnet 3, then by an eccentric shaft 52, for said first cap 31, and by a second shaft 321, which forms the axis of rotation of said permanent magnet 3 only, for said second cap 32.

A casing 34 comprising first 343 and second 344 parallel and cylindrical cavities receives, in said first cavity 343, both of the first 31 and second 32 caps and said permanent magnet 3, said second shaft 321 of said second cap 32 firstly, which is lodged in a bore 341 at the bottom of said first cylindrical cavity 343. A washer 33, whose external diameter corresponds to the internal diameter of said first cylindrical cavity 343 and whose internal diameter corresponds to that of said first shaft 311, is placed around said first shaft 311 and serves as a bearing.

Said second cylindrical cavity 344 of said casing 34 receives, through an assembly bore 342 situated at the end where said second shaft 321 of said second cap 32 is placed, the tubular end of said first part 1 of said first preferred embodiment of the device according to the invention. A cylindrical surface 13 of said first part 1 with a diameter slightly greater than the diameter of said assembly bore 342 blocks said first part 1 in said casing in such a way that only a cylindrical surface of friction 14 situated at the end of said first part 1 emerges in said second cylindrical cavity 344.

The two caps 31, 32, the casing 34 and said washer 33 thus constitute the means of connection, between said permanent magnet 3 and said first part 1, which allow said permanent magnet 3 a degree of freedom of rotation substantially about one of its main axes of inertia perpendicular to its direction of magnetization.

At the opposite end from the one where it receives said first part 1, said second cylindrical cavity 344 of said casing 34 receives, in sequence and engaged one behind the other, a retaining spring 44, a nut constituting said output shaft 42, a driving free-wheel spring 43, then said input shaft 41 formed by a tube segment whose interior 411 is able to slide and turn on said screw 62 and whose outer surface is able to cooperate with said driving free-wheel spring 43, which also cooperates with an analogous surface situated on said nut 42 in order to form said free-wheel means 43 for driving said output shaft 42 in said first direction when said input shaft 41 turns in said first direction.

Said retaining spring 44 cooperates with said cylindrical friction surface 14 situated at the end of said first part 1, and with an analogous surface situated on said nut 42, in order to form said retaining means for preventing rotation of said output shaft 42 in the direction opposite to said first direction.

The details and operation of this system of friction springs are described in full in the document WO/2004/019796 and will therefore not be explained in more detail here. This system adequately meets the objectives of the present invention but may of course also be replaced by any type of free-wheel system, for example free wheels with needles.

Said nut 42 cooperates, by way of its inner thread 61, with the screw 62 constituting said transmission means, such that the rotation of said output shaft 42 causes the displacement of said second part 2 relative to said first part 1.

A lever 51 integral with said input shaft 41, whose axis of rotation it shares, formed in this first preferred embodiment of the device by said screw 62, comprises a supporting groove 511 whose width is greater than or equal to the diameter of said eccentric shaft 52 with which it cooperates to form said step-down gears for transforming the movements of said permanent magnet 3 into rotation of said input shaft 41 alternately in a first direction and in the opposite direction, with a gear reduction ratio between the rotation of said input shaft 41 and that of said permanent magnet 3 and such that a change of direction of rotation of said permanent magnet 3 causes the change of direction of rotation of said input shaft 41.

A closure piece 71, comprising a bore 711 for allowing said second part 2 to pass through, closes the casing once the rest of the assembly work has been completed.

Figure 3:
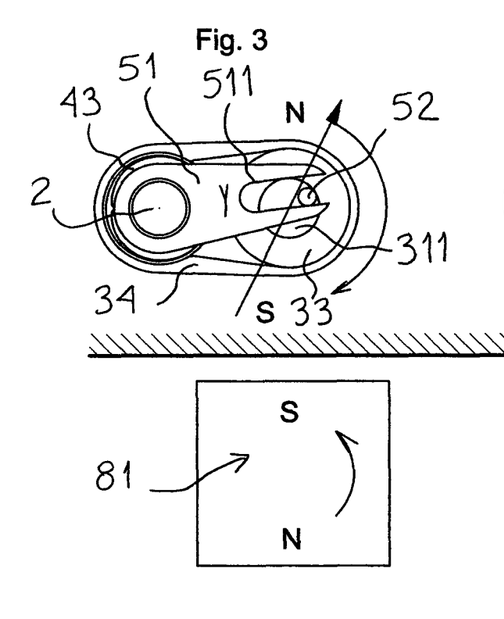
FIGS. 3 to 6 show views along the axis of rotation of said permanent magnet in which the device is shown without some of its components, so as to illustrate said lever in four different states in the presence of a magnetic field source placed outside the body.
Figure 4:
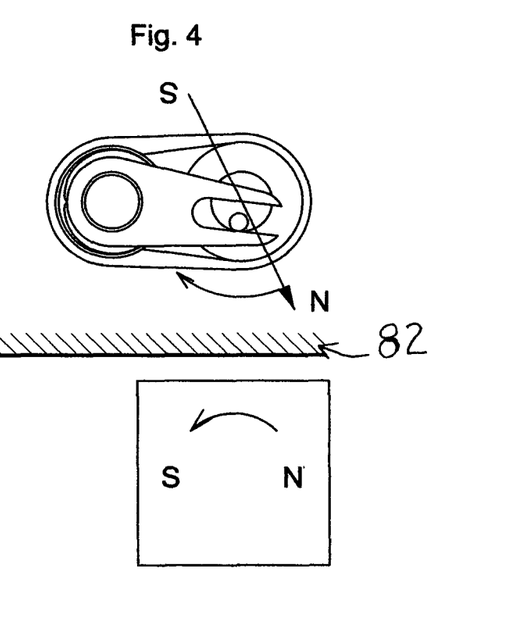
Figure 5:
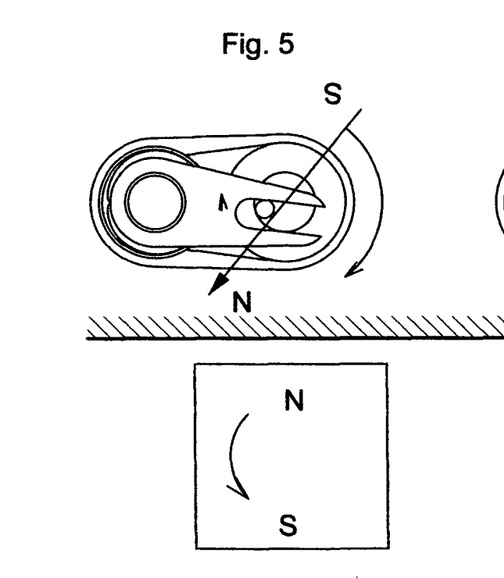
Figure 6:
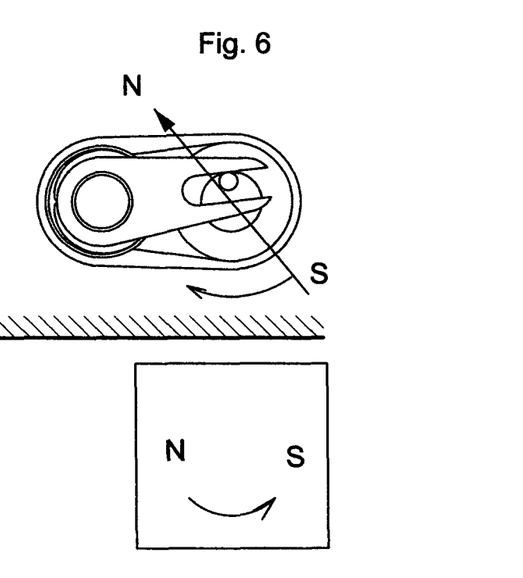

The functioning of said gear reduction means is shown in detail in FIGS. 3 to 6 where the arrows indicate the movement that will be produced under the effect of the depicted position of the magnetic field source 81 placed outside the body which it is supposed it has just been given. The limits 82 of the body are symbolized in said figures by a solid line representing the skin, and with cross-hatching representing the inside of the body. FIG. 3 shows the start of a movement period where said lever 51 will be driven by said eccentric shaft 52 which has come into contact with the supporting groove 511 in the direction of the hands of a clock in said first direction up to a maximum displacement of said lever in this first direction represented in FIG. 4. Between FIG. 4 and FIG. 5, the permanent magnet continues its rotation in the direction of the hands of a clock but without driving the lever 51, on account of the greater width of the supporting groove 511 compared to the diameter of said eccentric shaft 52, until said eccentric shaft 52 comes into abutment against the face opposite the one it has left of the supporting groove 511 and a new movement period starts which leads to the maximum position of the lever 51 in the direction opposite to said first direction represented in FIG. 6. A new sector of rotation of the permanent magnet 3 follows during which said lever 51 is not driven, and the system resumes the position shown in FIG. 3 before starting a new cycle. The relative position of the respective directions of magnetization of said permanent magnet 3 and of said magnetic field source 8 placed outside the body dictates the intensity of the forces that can be transmitted from one to the other. If one wishes to actuate efficiently said first preferred embodiment of the device according to the invention with the aid of a neodymium magnet placed outside the body at the point closest to said permanent magnet 3, the existence of sectors in which the rotation of the permanent magnet 3 does not drive the lever 51 makes it possible to use the rotation of the permanent magnet 3 to elongate said device or reset it only in the sectors where the strength of the torque applied to it is sufficient to effect these motive forces.

Reference will now be made to FIGS. 7 to 12 which show a second preferred embodiment of the device according to the invention designed more particularly for implantation in the medullary canal of a long bone in order to permit bone elongation or movement. In this second preferred embodiment, said first part 1 is composed substantially of a tube 10 which, at a first end, comprises a cylindrical cavity 15 with a diameter greater than that of the rest of the inside of said tube 10 and which ends with an annular supporting surface 152 and at least one longitudinal inner groove 151 substantially of the same length as said cylindrical cavity 15. Approximately at the end opposite said first end, at least one bore forming an angle of between 30 and 90° with respect to the axis of said tube 10 constitutes said first means 11 of connection to the body. Said second part 2 is substantially a cylinder 20 able to cooperate with the small diameter of said tube 10. Said second means 21 of connection to the body are composed of at least one bore substantially perpendicular to the axis of said cylinder 20. Oblong longitudinal cuttings 16 are made in said tube 10 to permit locking in said second means 21 of connection and the subsequent elongation.

Figure 7:
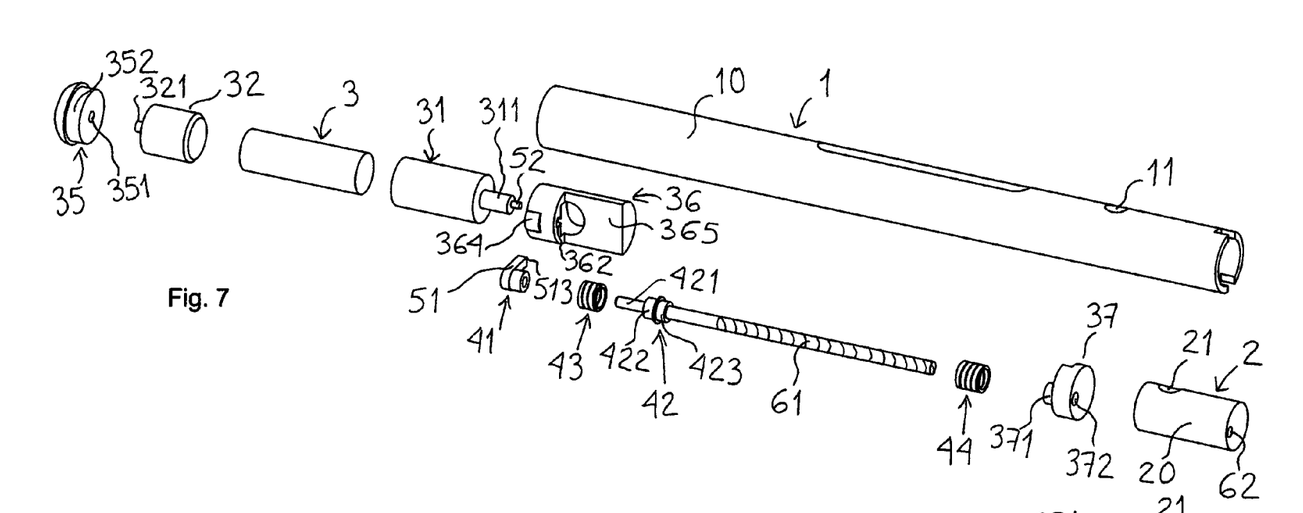
FIGS. 7 and 8 are exploded perspective views of this second embodiment at two different angles.
Figure 8:
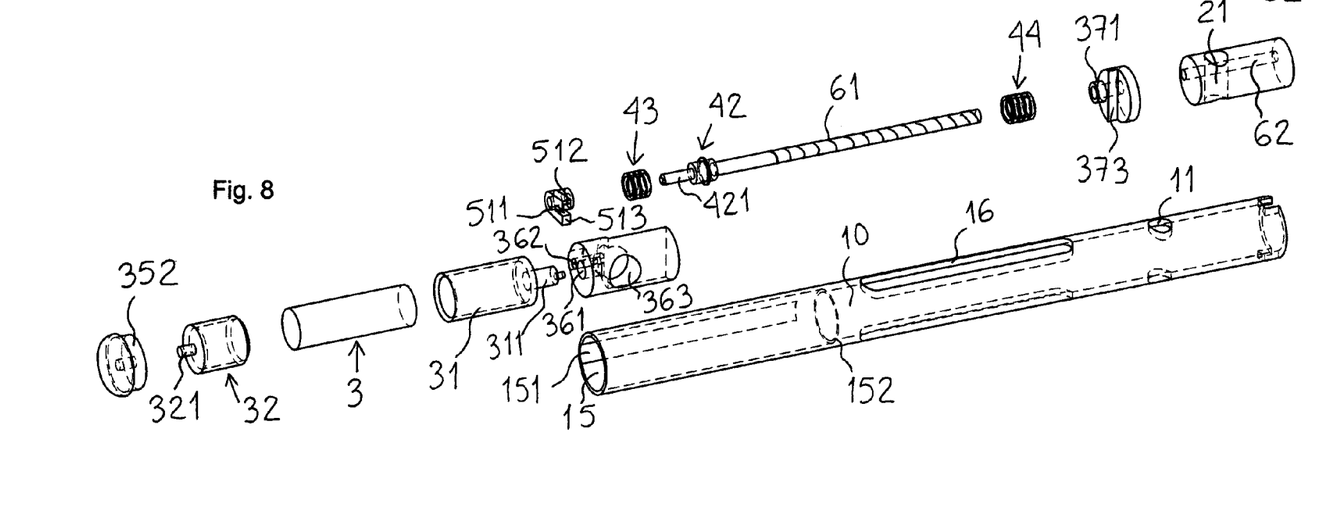

As in said first preferred embodiment of the device according to the invention, the permanent magnet 3 is cylindrical, magnetized diametrically and bonded, for example with the aid of a silicone adhesive, to the inside of first 31 and second 32 caps which are arranged head to tail and which, at the opposite end from the one in which said permanent magnet 3 is inserted, are continued, respectively, by a first shaft 311, which forms the axis of rotation of said permanent magnet 3, then by an eccentric shaft 52, for said first cap 31, and by a second shaft 321, which forms the axis of rotation of said permanent magnet 3 only, for said second cap 32. In addition, a lever 51 integral with an input shaft 41, whose axis of rotation it shares, comprises a supporting groove 511 whose width is greater than or equal to, but preferably equal to in this second preferred embodiment, the diameter of said eccentric shaft 52 with which it cooperates to form said step-down gears.

The output shaft 42 comprises two cylindrical surfaces, one of which 422 is designed to receive said driving freewheel spring 43 and, while the other 423 is designed to receive said retaining spring 44 and, affixed to the first, a shaft 421 which constitutes the axis of rotation of said input shaft 41, and, affixed to the second, a screw 61 which cooperates with an internal thread 62 parallel to the axis of said second part 2 in order to constitute said transmission means, such that the rotation of said output shaft 42 causes the displacement of said second part 2 relative to said first part 1.

A support 36 whose outer surface is substantially cylindrical, and which is able to cooperate with said cylindrical cavity 15, except for a protuberance 364 for cooperating with said longitudinal inner groove 151 of said tube 10 to ensure the blocking in rotation of said support 36 relative to said tube 10, receives and maintains in a suitable relative position the following:

said first shaft 311 for which it serves as a bearing in a first axial bore 361, the shaft part 421 of said output shaft 42 in a second bore 362 parallel to said first bore 361, said input shaft 41 having been first engaged on this shaft part 421, the lever 51 in a third bore 363 perpendicular to said first 361 and second 362 bores, the surface of said third bore 363 limiting the rotation of said lever 51 whose ends 512 and 513 come into abutment, respectively, against said third bore 363 when the lever 51 turns in said first direction or turns in the opposite direction to said first direction. The whole assembly constituting first abutment means in one direction and second abutment means in the opposite direction, in order to limit the rotation of said permanent magnet 3 to an angle sector of less than 180°, if the dimensions of said lever 51 and of said third bore 363 are suitably chosen.

The gear reduction ratio of this second preferred embodiment of the device according to the invention depends on the distance between said first bore 361 and said second bore 362, on the one hand, and on the eccentricity of said eccentric shaft 52, on the other.

A stopper 35, provided with an axial bore 351 which receives said second shaft 321 for which it serves as a bearing, is engaged with a force fit on said first end of said tube 10 by way of a cylindrical surface 352 with a diameter slightly greater than that of said cylindrical cavity 15.

A supporting component 37, which is sited at the bottom of said cylindrical cavity 15 in abutment against said annular supporting surface 152 and is blocked in rotation by its longitudinal plane surface 373 being in contact with another longitudinal plane surface 365 of said support 36, also has a cylindrical friction surface 371 able to cooperate with the retaining spring 44 in order to form said retaining means for preventing the rotation of said output shaft 42 in the direction opposite to said first direction. This supporting component 37 also supports all the weight applied by the patient on the elongation nail and transferred by way of said second part 2, of said screw 61, which works in traction, and of the part of said output shaft 42 that is in contact with said supporting component 37.

Figure 9:
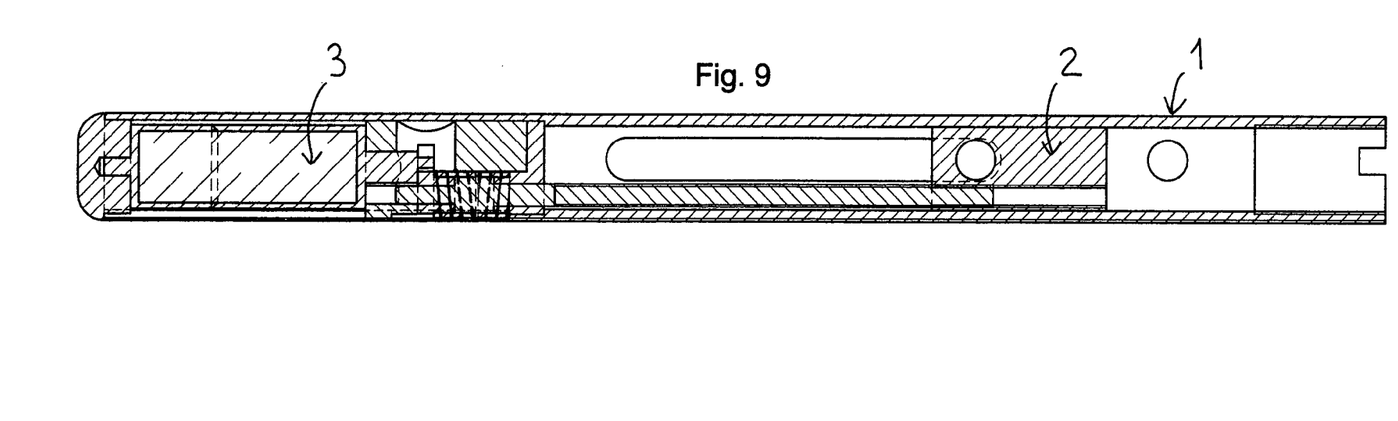
FIG. 9 shows said second preferred embodiment of the device according to the invention in its initial position.
Figure 10:
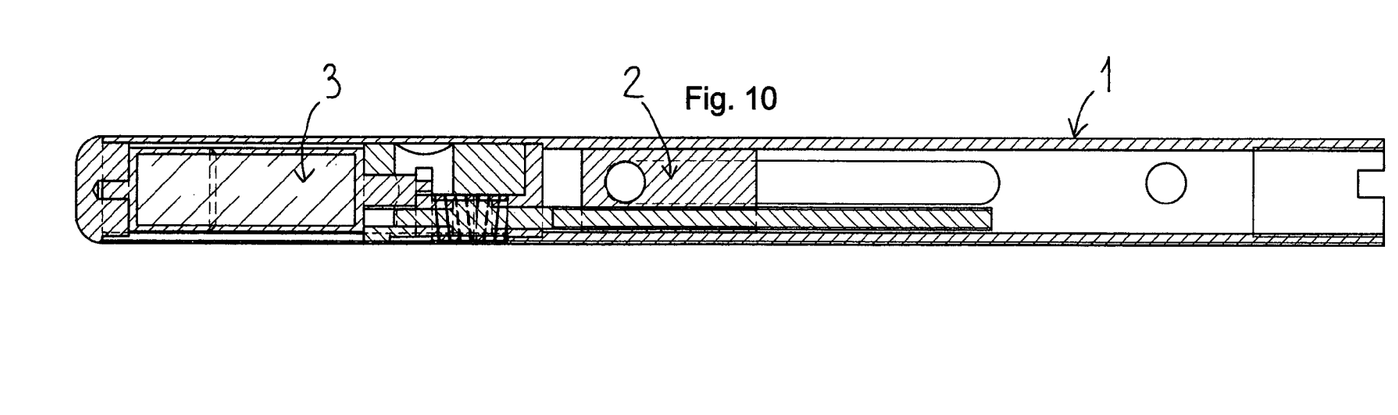
Figure 11:
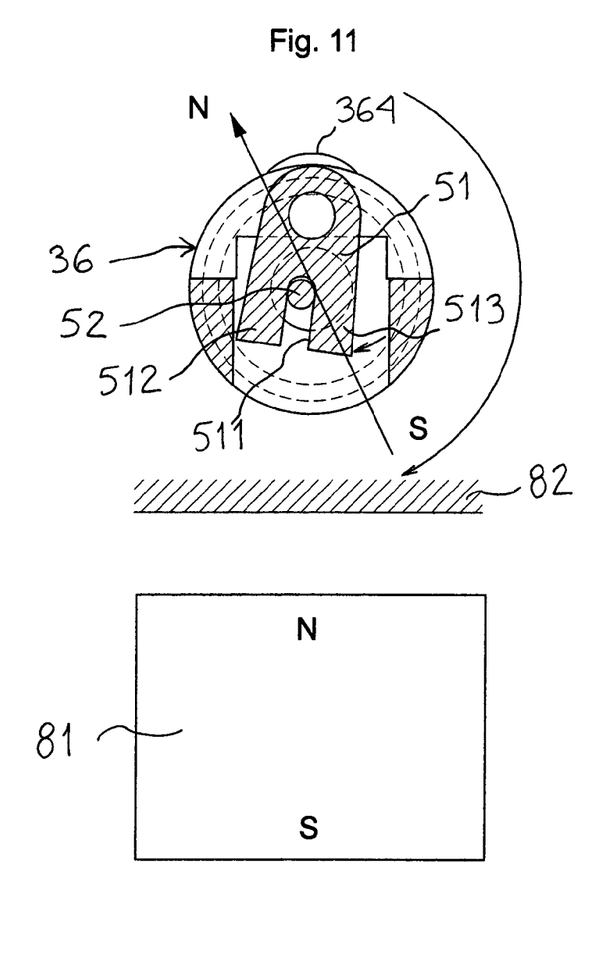
FIGS. 11 and 12 are cross sections, of said second preferred embodiment, passing through said lever and showing two states of said device in the presence of a magnetic field source placed outside the body.
Figure 12:
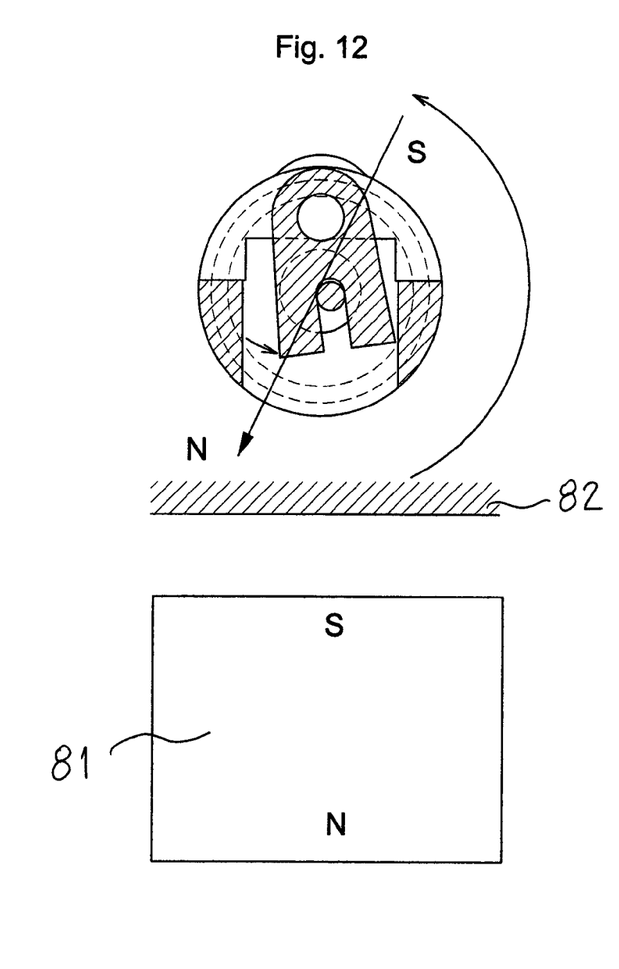

The functioning of this second preferred embodiment of the device according to the invention is very similar to that of said first preferred embodiment of the device according to the invention and will not therefore be explained in detail. FIGS. 9 and 10 show the displacement of said second part 2 relative to said first part 1 between the time when the elongation nail is implanted (FIG. 9) and the end of elongation (FIG. 10). FIGS. 11 and 12 show the abutment positions of said lever 51 and the directions of magnetization of said permanent magnet 3 that are obtained under the effect of a magnetic field source 81 placed outside the body. In these figures, the curved arrows indicate the already effected rotations of the direction of magnetization of said permanent magnet 3 and of said lever 51 for arriving at the abutment position shown and not the movement that will be performed. These arrows are more or less on the scale of the rotations performed and thus illustrate the gear reduction ratio of the device according to the invention. Said figures show stable states, and the position of said magnetic field source 81 has to be modified, for example by turning it, such that these develop toward the state shown in the other figure.

Figure 13:
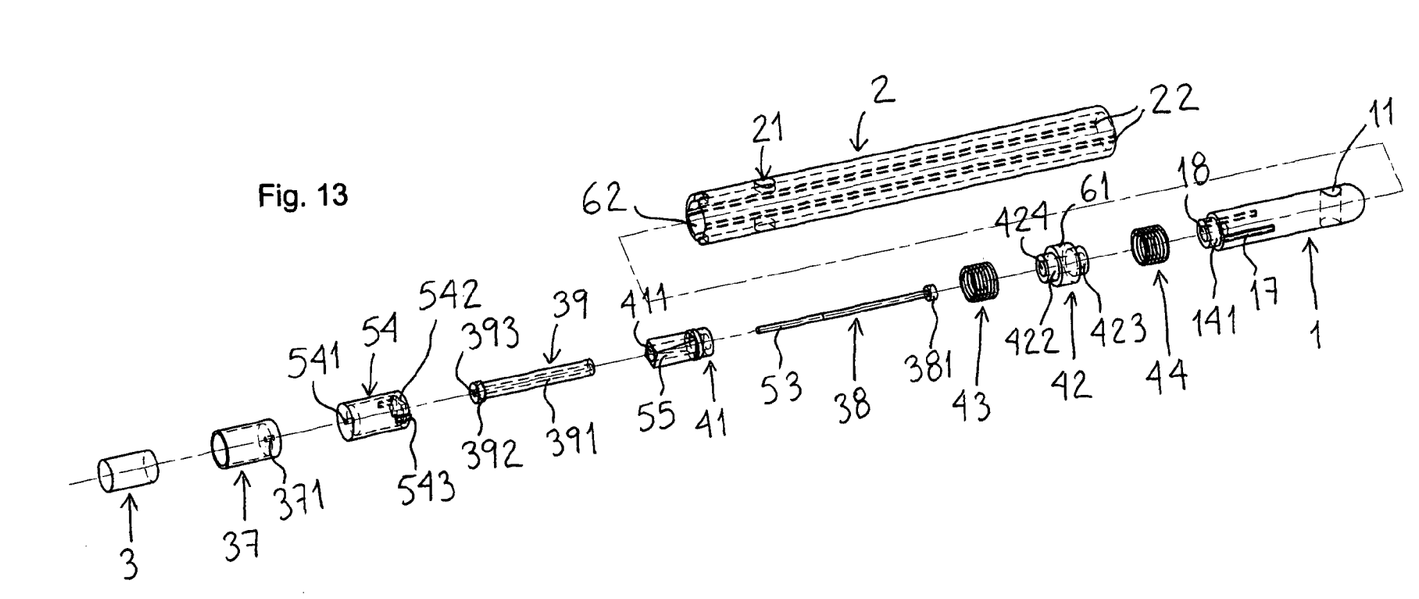
FIG. 13 shows an exploded perspective view of said third embodiment.
Figure 14:
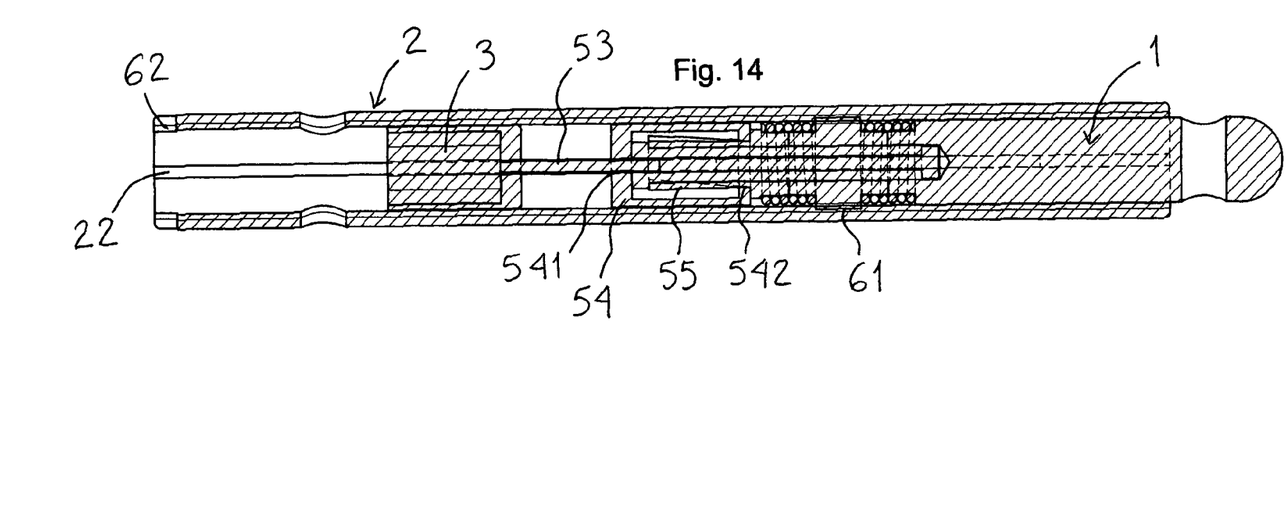
FIG. 14 shows a cross section, of said third preferred embodiment, passing through the axis of rotation of said permanent magnet.

The third preferred embodiment of the device according to the invention shown in FIGS. 13 and 14 and to which reference is now made is particularly advantageous when a very high gear reduction ratio is sought within a particularly small diameter and when, by contrast, sufficient length is available. However, the control of this third preferred embodiment may be awkward if it has to be done manually.

The first part 1 of said third preferred embodiment of the device according to the invention is substantially a cylinder with a rounded end which also has at least one bore substantially perpendicular to the axis of said first part 1 and which constitutes said first means 11 of connection to the body. Situated at the opposite end from said rounded end, and arranged radially with respect to the surface of said cylinder, there are anti-rotation fins 17 and, forming the continuation of said cylinder and sharing its axis, there is a cylindrical surface 141 for cooperating with a retaining spring 44 and a cylindrical seat 18 which opens out at the end of said cylindrical surface 141 opposite from the one joining it to said cylinder.

The second part 2 of said third preferred embodiment of the device according to the invention is a tube completely threaded on its inner face 62 in which said first part 1 is able to move freely in translation but without excessive play. Anti-rotation grooves 22 for cooperating with said anti-rotation fins 17 of said first part 1 in such a way as to prevent the rotation of one relative to the other are cut out longitudinally inside said second part 2. More or less at one end of said second part 2, at least one bore forming an angle of 30 to 90° with the axis constitutes said second means 21 of connection to the body.

The permanent magnet 3 is cylindrical, magnetized diametrically and bonded, for example with the aid of a silicone adhesive, to the inside of a cap 37 which, at the end opposite from the one in which said permanent magnet 3 is introduced, has an internal thread 371 which receives a screw 38 with a threaded part 53, or fourth surface, and a head 381 and which is welded at the end remote from its head 381 inside said cap 37 before bonding of said permanent magnet 3. Said screw 38 constitutes the axis of rotation of said permanent magnet 3 to which it is fully connected. The head 381 of said screw 38 is accommodated in said cylindrical recess 18 of said first part 1. Its body is introduced into the central channel 393 opening out at each end from an assembly shaft 39 which comprises a cylindrical body 391 whose diameter is slightly greater than that of said cylindrical recess 18, and a head 392 and on which have previously been mounted in succession said input shaft 41 against the head 392, then said driving free-wheel spring 43, said output shaft 42 and said retaining spring 44. The end of said cylindrical body 391 opposite from said head 392 is assembled with a force fit in said cylindrical recess 18, blocking said screw 38 and thus said permanent magnet 3 in translation but not in rotation with respect to said first part 1 and keeping the elements that have been previously mounted on said cylindrical body 391 joined to one another.

Said output shaft 42 comprises two cylindrical surfaces, one of which 422 is designed to receive said driving free-wheel spring 43, while the other 423 is designed to receive said retaining spring 44, and they are arranged on either side of a screw 61 for cooperating with the threaded inside 62 of said second part 2. The center of said output shaft 42 comprises a bore 424 that allows said output shaft 42 to be mounted freely in rotation on said assembly shaft 39. All these elements are coaxial.

At one end, said input shaft 41 has a cylindrical surface designed to receive said driving free-wheel spring 43 and, at the other end, it has a torsade 55, or sixth surface. It also has a bore 411 which extends along its axis and which allows it to be mounted freely in rotation on said assembly shaft 39.

This third preferred embodiment of the device according to the invention additionally comprises a substantially cylindrical amplifying component 54 able to slide in said second part 2 and which comprises anti-rotation fins 543 able to cooperate with said anti-rotation grooves 22 of said second part 2, which is itself blocked in rotation with said first part, and, at one end, an inner thread 541, or third surface, able to cooperate with the threaded part 53 of said screw 38 and, at the other end, female surfaces 542, or fifth surface, able to cooperate with said torsade 55. This amplifying component 54 is screwed onto said threaded part 53 of said screw 38 after said assembly shaft 39 has been mounted with a force fit in said first part 1 and before said cap 37 is screwed onto said screw 38 and the two welded together.

This third preferred embodiment of the device according to the invention operates in the following way. A rotating magnetic field created by the magnetic field source placed outside the body sets said permanent magnet 3 in rotation in a first direction for a number of revolutions, the maximum number of which is fixed by the length and the pitch of the threaded part 53 of the screw 38 or by the space reserved for the amplifying component 54 for its translation between the abutments formed by the cap 37 on the one hand and by the head 392 of said assembly shaft 39 on the other. The rotation of said permanent magnet 3 causes that of said screw 38 to which it is connected and which, by way of the threaded part 53 of the screw, cooperates with the inner thread 541 of said amplifying component 54 in order to constitute said second helical connection, the translation of said amplifying component 54 in a first direction of translation. The amplifying component being blocked in rotation by the anti-rotation fins 543 and cooperating by way of its female surfaces 542 with said torsade 55 drives said input shaft 41 in rotation in a direction that is of course also dependent on the pitch of said torsade 55. Said permanent magnet 3 is then set in rotation in the direction opposite to said first direction for a number of revolutions identical to the number effected in said first direction, and said input shaft 41 recovers its initial position as a result of the reverse movement of all the components. During these movements, the system of friction springs works and drives said output shaft 42 in rotation in only one direction, which obviously leads to the displacement of said second part 2 relative to said first part 1.

This cycle is repeated as many times as is necessary for obtaining the desired elongation. The gear reduction ratio of this third preferred embodiment of the device according to the invention depends on the pitch of said threaded part 53 of said screw and of said torsade 55. In addition, the pitch of said torsade 55 must be sufficiently great with respect to the existing friction in order to allow said device to function.

In this third preferred embodiment of the device according to the invention it is also possible to position a crosswheel between the permanent magnet 3 and the screw 53 to make it easier, if so desired, to control said device by rotating a magnetic field source 81 outside the body around an axis parallel to the axis of rotation of said permanent magnet 3 and placed closest to said permanent magnet 3. The use of a crosswheel in fact ensures that said permanent magnet 3 drives the input shaft 41 only over a portion of its rotation for which the torque that can be exerted on said permanent magnet 3 by said magnetic field source 81 is elevated by virtue of judicious adjustment of the direction of magnetization of said permanent magnet 3 with respect to the direction in which the magnetic field source 81 is placed and to the position of the wheel which is integrally connected to said permanent magnet 3 and drives the crosswheel, integral with said screw 53, with respect to said crosswheel. A good result is obtained if the bisecting line of the direction of magnetization of said permanent magnet 3 when said driving free-wheel begins meshing with said crosswheel and the direction of magnetization of said permanent magnet 3 when said driving wheel leaves said crosswheel is substantially perpendicular to the direction in which said magnetic field source 81 can be placed closest to said permanent magnet 3.

The device according to the invention is advantageously made of materials that are mechanically robust and well tolerated by the body, such as stainless steels, for example 316L, titanium alloys or, preferably, high-performance alloys based on chromium and cobalt, such as Phynox, for example. Said permanent magnet 3 is advantageously a neodymium magnet of the type whose Curie temperature is greater than 150° C. in order to permit sterilization of said device according to the invention by all possible means, particularly with superheated steam at 134° C., without risk of damage to said permanent magnet 3.

The surfaces of said device according to the invention that are subjected to friction advantageously receive a surface treatment that reduces their coefficient of friction and is based on adamantine amorphous carbon or tungsten disulfide, for example.

Although the use of a cylindrical permanent magnet 3 that is magnetized diametrically has been described and is preferred, any magnet geometry is conceivable, in particular parallelepipedal, of hexagonal cross section, etc, with any direction of magnetization.

The device according to the invention is implanted and fixed inside the body in a manner that is entirely known and that is similar to devices not equipped with an elongation mechanism.

Industrial Applicability

The present invention is particularly useful for any type of intracorporeal elongation device, such as prostheses allowing bone growth, intramedullary nails for elongation or movement of bone, spinal distraction or compression rods, or bone distractors or intercostal distractors. It can also be used to produce growth plates for correcting bone deformations or pumps implanted for progressive and controlled diffusion of substances within the body and, more widely, can be used to produce any type of device whose geometry is to be modified in a gradual and controlled way without direct contact.

The invention claimed is:

1. An intracorporeal elongation device comprising:
   a first part including first means of connection to the body;
   a second part including:
      second means of connection to the body; and
      a permanent magnet;
      wherein the second part is mounted so as to slide relative to the first part;
   means of connection between the permanent magnet and the first part, which means of connection allow the permanent magnet one rotational degree of freedom substantially about one of its main axes of inertia and perpendicular to its direction of magnetization;
   an input shaft;
   step-down gears for transforming the movements of the permanent magnet into rotation of the input shaft, alternately in a first direction and in the opposite direction, with a gear reduction ratio between the rotation of the input shaft and that of the permanent magnet and such that a change of direction of rotation of the permanent magnet causes the change of direction of rotation of the input shaft, the step-down gears including:
      a first supporting surface that is substantially cylindrical and affixed to the permanent magnet, but is not coaxial with the permanent magnet's one rotational degree of freedom; and
      a lever that is affixed to the input shaft and defines a groove that is sized and shaped to receive the first supporting surface, the width of the groove being substantially equal to the diameter of the first supporting surface;
   an output shaft;
   free-wheel means for driving the output shaft in the first direction when the input shaft turns in the first direction;
   retaining means for preventing the rotation of the output shaft in the direction opposite to the first direction when the input shaft turns in the direction opposite to the first direction; and
   transmission means by which the rotation of the output shaft causes the displacement of the second part relative to the first part.

* * * * *